US012758141B2

(12) United States Patent
Whiting et al.

(10) Patent No.: US 12,758,141 B2
(45) Date of Patent: Oct. 13, 2026

(54) CRS DETECTION AND PREDICTIVE VITALS

(71) Applicant: Current Health Inc., Richfield, MN (US)

(72) Inventors: Stewart Whiting, Edinburgh (GB); Matthew Wilkes, Edinburgh (GB); Nicholas Calafat, Richfield, MN (US); Nicole Zahradka, Richfield, MN (US)

(73) Assignee: Current Health Inc., Richfield, MN (US)

( * ) Notice: Subject to any disclaimer, the term of this patent is extended or adjusted under 35 U.S.C. 154(b) by 0 days.

(21) Appl. No.: 18/541,500

(22) Filed: Dec. 15, 2023

(65) Prior Publication Data

US 2025/0194991 A1 Jun. 19, 2025

(51) Int. Cl.
*A61B 5/00* (2006.01)

(52) U.S. Cl.
CPC .............. *A61B 5/41* (2013.01); *A61B 5/4857* (2013.01); *A61B 5/6804* (2013.01); *A61B 5/7264* (2013.01); *A61B 5/746* (2013.01)

(58) Field of Classification Search
CPC ....... A61B 5/41; A61B 5/4857; A61B 5/6804; A61B 5/7264; A61B 5/746
See application file for complete search history.

(56) References Cited

U.S. PATENT DOCUMENTS 11,645,745 B2 5/2023 Wei
2015/0025329 A1 1/2015 Amarasingham
2017/0150893 A1 6/2017 Mccombie
2019/0320910 A1 10/2019 Nakajima
2019/0350535 A1 11/2019 Zhao
2020/0397972 A1 12/2020 Ku
2021/0077035 A1* 3/2021 Kayser ................ A61B 5/7225
2023/0304695 A1 9/2023 Desai
2024/0032853 A1* 2/2024 Sekaric ............... A61B 5/7275

OTHER PUBLICATIONS

Rajeeve, Sridevi, et al., Care Delivery and Regulatory Policy, "Early Detection of CRS After CAR-T Therapy Using Wearable Monitoring Devices: Preliminary Results in Relapsed/Refractory Multiple Myeloma (RRMM)", American Society of Clinical Oncology (ASCO), copyright 2023, Publication e13626, 1 page.

Rajeeve, Sridevi, et al., "Early Detection of CRS After CAR-T Therapy Using Wearable Monitoring Devices: Preliminary Results in Relapsed/Refractory Multiple Myeloma (RRMM)", American Society of Clinical Oncology (ASCO) Abstract No. 409954, Feb. 13, 2023, 3 pages.

* cited by examiner

*Primary Examiner* — Tammie K Marlen
(74) *Attorney, Agent, or Firm* — Sheppard Mullin Richter & Hampton LLP

(57) ABSTRACT

The present technology provides for a remote continuous monitoring system that monitors a patient's vital signs and generates an alarm in response to detecting a likely onset of an adverse event. The monitoring system advantageously allows patients recovering from clinical treatments to do so at home, outside of a hospital. Furthermore, the monitoring system provides continuous monitoring of patient vital signs, which advantageously provides more information than intermittent manual measurements of patient vital signs typical in a hospital. The monitoring system, therefore, may more readily and more timely detect a likely onset of an adverse event.

21 Claims, 7 Drawing Sheets

CRS DETECTION AND PREDICTIVE VITALS

FIELD OF THE INVENTION

The present technology relates to a remote continuous monitoring system for detecting and generating notifications upon detection of the likely onset of cytokine release syndrome (CRS), neurotoxicity (e.g., immune effector cell-associated neurotoxicity syndrome (ICANS)), and other adverse events.

BACKGROUND

Immunotherapy is a type of treatment that uses the patient's immune system to target cancer cells more efficiently. There are several types of cancer immunotherapies, including CAR-T therapy and bispecific T cell engagers (BiTEs). They are typically used to treat blood cancers, including relapsed or refractory leukemias, lymphoma and multiple myeloma.

While immunotherapies such as these are useful for treating various cancers, these treatments may cause serious side effects. For example, key side effects of immunotherapies include cytokine release syndrome (CRS) and immune effector cell-associated neurotoxicity syndrome (ICANS). CRS is a systemic inflammatory response that can occur when activated T-cells release large amounts of cytokines (small messenger proteins) into the bloodstream. The release of cytokines can lead to symptoms progressing from fever to low blood pressure, difficulty breathing, and multi-organ dysfunction. Other side effects may occur.

The side effects can be life threatening if not timely detected and treated. Prompt treatment of CRS typically involves medications, such as corticosteroids or tocilizumab, that help suppress the immune response and reduce inflammation. In severe cases, patients may require admission to an intensive care unit and supportive care, such as oxygen, mechanical ventilation, and hemodynamic support.

Vital signs, such as temperature, blood pressure, heart rate, and respiratory rate, are critical indicators of a person's health status, and core to the diagnosis of CRS. Traditionally, patients are confined to remaining in the hospital or other treatment facility, to facilitate vital sign monitoring and treatment if necessary. However, traditional vital sign monitoring methods rely on periodic manual measurements by healthcare staff, which can lead to delays in detecting the onset of CRS.

The current methods of monitoring are inefficient for these and other reasons. Due to the need for prompt treatment in the event adverse side effects are detected, remote monitoring is typically not used with theses patients. Prior remote monitoring systems are not specifically designed to promptly detect events that may indicate adverse effects of immunotherapies. Due to the general nature of prior remote monitoring systems (not specifically designed to detect adverse effects of immunotherapies), they can either detect adverse events too late or generate too many false positives (e.g., erroneous indication that an adverse event has occurred.) This confines a patient to a hospital for the period when they are at risk (up to two weeks, in some cases). This is inconvenient for the patient and increases the costs significantly.

These and other drawbacks exist in this context.

SUMMARY

Various aspects of the present technology can a remote, continuous monitoring system with at least one sensor that monitors specific vital signs of an immunotherapy patient to promptly detect events that may indicate adverse events (e.g., CRS, ICANS) of immunotherapies and provide a notification. Additionally, due to the fact that certain relevant parameters may vary by person, the system can be configured to determine a baseline for an individual patient. This enables to system to implement more sensitive/specific rules-based alarm recommendations, based on each individual patient's baseline vital signs without triggering undue false positives. This enables setting/adjusting alarm thresholds to a specific patient given their baseline/clinical history/expected risk.

Additionally, the system may use predictive alarming as detailed below. The predictive alarming can enable the establishment of criteria (which may be patient specific), by the system and/or in conjunction with input from the physician, to generate an alert if there was a certain probability (e.g., a 70% probability) that CRS (or other adverse event) would be detectable within a predetermined time (e.g., in the next 4 hours). The probability and/or time can be systems generated based on a set of rules, prior data and/or physician input. This predictive alarming allows early enough notification for an individual patient to receive treatment to stop progression of the disease without undue false alarms. This helps the physician better balance the risks and benefits of prophylactic therapy for CRS.

The combination of these and other features of the remote, continuous monitoring system with patient-specific baselines and thresholds enables immunotherapy patients to be released from the hospital, while being continuously monitored for adverse events, where the continuous monitoring technology can detect evidence of adverse events sooner than with manual, periodic testing by standard nursing care, all while leveraging personalized thresholds and avoiding false positives.

The remote monitoring system advantageously allows patients recovering from immunotherapy, or other clinical treatments, to do so at home and outside a hospital. Furthermore, the monitoring system provides continuous monitoring of patient vital signs, which advantageously provides more information than intermittent manual measurements of patient vital signs typical in a hospital. The monitoring system, therefore, may more readily and more timely detect a likely onset of an adverse event.

In one aspect of the present technology, the remote continuous monitoring system can remotely and continuously monitor patient vital signs through one or more wearable sensors. For example, a patient can wear an axillary sensor that adheres to the patient's skin with an adhesive patch, or the patient can wear an armband sensor that is held against the patient's skin by an armband. The wearable sensors can measure patient vital signs, such as temperature, blood pressure, heart rate, respiratory rate, and the like. The monitoring system can determine a baseline for patient vital signs based on measurements of the patient vital signs via the wearable sensors. The monitoring system can detect a likely onset of an adverse event based on one or more patient vital signs measured by the wearable sensors deviating from the baseline, such as by exceeding a corresponding vital sign threshold. The vital sign thresholds can be based on default values, personalized values, values derived from the patient's baseline vital signs, values derived from patient's biorhythm patterns, values derived from time series modeling of the patient's vital signs, and other approaches further described herein.

In one aspect of the present technology, the remote continuous monitoring system can generate one or more notifications in response to detecting a likely onset of an adverse event. For example, the monitoring system can generate an alarm when a patient vital sign exceeds a corresponding vital sign threshold. In some instances, the monitoring system can generate one or more notifications in response to detecting an error, such as loss of connectivity with the wearable sensors, loss of connectivity to the Internet, loss of measurements from the wearable sensors, unusual measurements from the wearable sensors, and the like. For example, unusual measurements from the wearable sensors, such as patient vital signs that are outside normal vital sign thresholds, can indicate the wearable sensors have been removed from the patient. In some instances, the monitoring system can generate a record of measurements from the wearable sensors that includes a log of any detected errors. The record of measurements can be useful for monitoring how the patient's vital signs fluctuate during a period of time (e.g., throughout a day, during a recovery period).

In one aspect of the present technology, the remote continuous monitoring system can apply an approach using default values to establish vital sign thresholds. For example, default values associated with recovery from a medical procedure can be provided by a medical authority. The monitoring system can set vital sign thresholds based on the default values. The monitoring system can generate one or more notifications in response to detecting that patient vital signs exceed the vital sign thresholds (e.g., the patient vital signs are outside default values).

In one aspect of the present technology, the remote continuous monitoring system can apply an approach using personalized values to establish vital sign thresholds. For example, personalized values for vital sign thresholds can be established based on baseline vital sign measurements of a patient. In this example, the vital sign thresholds can be a first predetermined amount above and a second predetermined amount below the patient's baseline vital sign measurements. The monitoring system can generate one or more notifications in response to detecting that patient vital signs exceed the vital sign thresholds (e.g., the patient vital signs are outside the personalized values). The personalized values for the vital sign thresholds can be adjusted to be more or less sensitive to account for natural variations in the patient's vital signs. The personalized values for the vital sign thresholds can be specific to a clinical scenario or reweighted for different clinical scenarios. For example, the personalized values can be adjusted based on a patient's clinical history, health risks, or other factors. The personalized values can be adjusted based on feedback from the patient or a healthcare service provider.

In one aspect of the present technology, the remote continuous monitoring system can detect changes in patient biorhythm patterns and generate one or more notifications in response to the changes. For example, a patient's vital signs can naturally fluctuate throughout the day. Temperature and heartrate, for example, may be lower at night while the patient is sleeping than during the day when the patient is awake. The monitoring system can establish the patient's baseline vital signs as a biorhythm pattern that follows the patient's baseline vital sign measurements throughout the day. The monitoring system can establish vital sign thresholds based on the biorhythm pattern. Because the vital sign thresholds are based on the biorhythm pattern, there may be instances where a patient vital sign measurement exceeds or does not exceed the corresponding vital sign threshold depending on the time of day. For example, the patient's baseline temperature as a biorhythm pattern can be higher during the day and lower at night. Vital sign thresholds based on the biorhythm pattern can be higher during the day and lower at night. In this example, a patient temperature measurement during the day may measure high and be within the temperature threshold for that time of day. Subsequent patient temperature measurements may also measure high and exceed the temperature threshold as the temperature threshold lowers in accordance with the patient's biorhythm pattern. The monitoring system can generate one or more notifications in response to the detecting that the patient's temperature exceeds the temperature threshold.

In one aspect of the present technology, the remote continuous monitoring system can apply an approach using a model that accounts for natural variations in the patient's vital signs and biorhythm patterns. For example, a machine learning model can be trained to generate vital sign thresholds based on baseline vital sign measurements. The patient's baseline vital sign measurements can be obtained through, for example, one or more wearable sensors. The baseline vital sign measurements can be provided to the machine learning model. In some instances, other factors such as the patient's clinical history, can be provided to the machine learning model. Vital sign thresholds for the patient can be determined based on the machine learning model. The machine learning model can generate vital sign thresholds as a function of time so that the vital sign thresholds follow the patient's biorhythm patterns throughout the day. The monitoring system can remotely and continuously monitor the patient's vital signs and generate one or more notifications in response to the detecting one or more of the patient's vital signs exceed the vital sign thresholds determined based on the machine learning model.

It should be understood the present technology can apply various approaches in various combinations to establish vital sign thresholds. For example, personalized values for vital sign thresholds can be applied to a patient biorhythm pattern so that the vital sign thresholds are a first predetermined amount above and a second predetermined amount below the patient's baseline vital sign measurements as they fluctuate throughout the day. Furthermore, the personalized values can be based on the patient biorhythm pattern so that the first predetermined amount above and the second predetermined amount below the patient's baseline vital sign measurements increase and decrease in accordance with the patient biorhythm pattern. For example, the first predetermined amount above and the second predetermined amount below the patient's baseline vital sign measurements can increase during the day when the patient is more active and decrease at night when the patient is resting. Many variations are possible.

In one aspect of the present technology, the remote continuous monitoring system can predict vital signs for the patient and generate one or more notifications based on the predicted vital signs exceeding corresponding vital sign thresholds. For example, the monitoring system can predict vital signs for the patient based on a machine learning model. The machine learning model can be trained to be specific to particular side effects (e.g., CRS, ICANS). The machine learning model can be trained to predict vital signs for the patient based on training data that includes historical vital sign data. The trained machine learning model can be applied to the patient's vital sign measurements. Based on the patient's vital sign measurements, the trained machine learning model can generate predicted vital signs for the patient. The monitoring system can generate one or more notifications in response to the predicted vital signs exceeding corresponding vital sign thresholds. This allows the monitoring system to predict that the patient may be experiencing or may be about to experience side effects.

For example, a general model can be trained using hours (e.g., 1.68 million hours) of vital sign data from various use cases, including CRS cases. The general model can be trained to predict vital signs up to several hours ahead of time. The general model can be weighted to be sensitive and specific to CRS using static and time-varying known categorical values and/or real values. These categorical values and/or real values can include critical blood based biomarkers, drug types, demographics, and vital sign data. Based on the general model, a physician can be alerted, for example, if a 70% probability of CRS will be detectable within the next four hours (e.g., 70% probability predicted vital signs will exceed corresponding vital sign thresholds within the next four hours), allowing the physician to provide early treatment to stop progression of CRS. As illustrated in this example, the present technology allows for prophylactic therapy for various side effects, including CRS.

In one aspect of the present technology, the remote continuous monitoring system provides for patient management outside of a medical facility (e.g., at home). The monitoring system can manage sensitivity and specificity of notifications (e.g., alarms) based on feedback from patients. The monitoring system can provide failsafe mechanisms to support patient care in cases where no notifications are generated, in cases where data flow is interrupted, and in cases where a notification is missed. The monitoring system can facilitate communication with healthcare service providers and provide appropriate notifications to the healthcare service providers as first line responders. The monitoring system can facilitate home delivery of treatments. For example, the monitoring system can facilitate home delivery of tocilizumab and steroids for treatment of CRS. The monitoring system can facilitate diagnosis and management of various health conditions, including CRS and ICANS. Furthermore, the monitoring system can facilitate patient interaction with the monitoring system. For example, the monitoring system can provide an interface that informs patients of their current health status, allows patients to confirm their health status, allows patients to provide additional information and feedback as to their condition, and allows patients to communicate with their caregivers and clinical teams.

In one aspect of the present technology, the remote continuous monitoring system can detect likely onset of adverse events (e.g., CRS, ICANS) in immunotherapy patients. For example, an immunotherapy patient can wear a wearable sensor for a period of time before undergoing an immunotherapy procedure. The immunotherapy patient's baseline vital signs can be obtained during this period of time. Based on the immunotherapy patient's baseline vital signs, vital sign thresholds can be determined for the immunotherapy patient. Subsequent to the immunotherapy procedure, the immunotherapy patient can be monitored through the wearable sensor. For example, the monitoring system can detect likely onset of side effects from the immunotherapy procedure when the immunotherapy patient's vital signs or predicted vital signs exceed corresponding vital sign thresholds. In response to a detection of likely onset of side effects, the monitoring system can alert the immunotherapy patient as well as healthcare service providers to respond appropriately. As illustrated in this example, the monitoring system provides remote and continuous monitoring of the immunotherapy patient, allowing the immunotherapy patient to recover at home.

It should be appreciated that many other features, applications, aspects, and/or variations of the present technology will be apparent from the accompanying drawings and from the following detailed description. Additional and/or alternative implementations of the structures, systems, non-transitory computer readable media, and methods described herein can be employed without departing from the principles of the present technology.

Figure 1A:
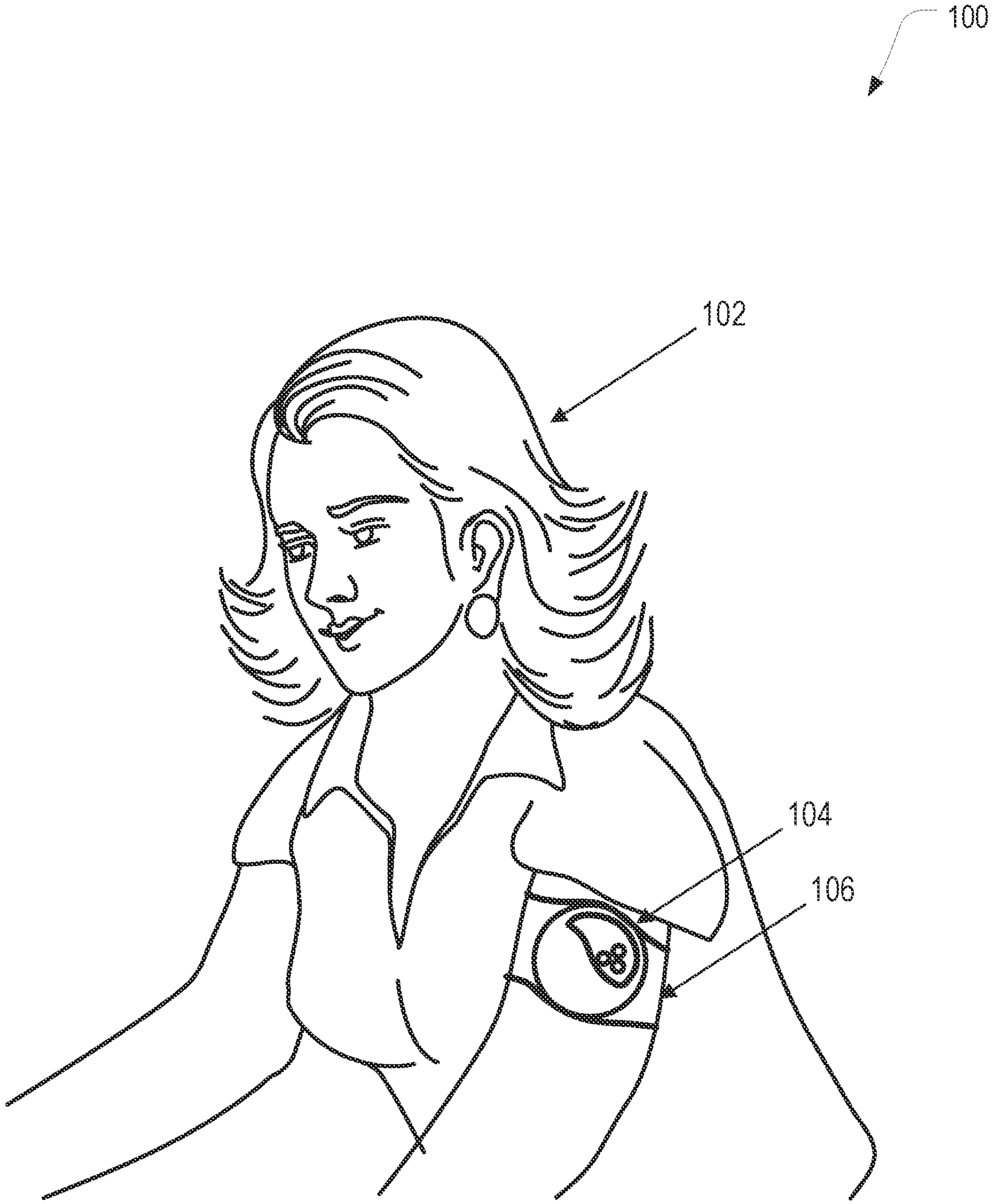
FIGS. 1A-1B illustrate examples of users with wearable sensors, according to various embodiments of the present technology.

The figures depict various embodiments of the present technology for purposes of illustration only, wherein the figures use like reference numerals to identify like elements. One skilled in the art will readily recognize from the following discussion that alternative embodiments of the structures and methods illustrated in the figures can be employed without departing from the principles of the present technology described herein.

DETAILED DESCRIPTION

Approaches for CRS Detection and Predictive Vitals

As background, patient health monitoring is critical to providing effective health services. Patient health monitoring can be especially critical for patients recovering from immunotherapy (e.g., CAR-T therapy, bispecific T cell engagers (BiTEs). CAR-T therapy and BiTEs may be used to treat blood cancers, such as relapsed or refractory leukemias and multiple myeloma. While immunotherapies such as these are useful for treating various cancers, these treatments may cause side effects. For example, key side effects of immunotherapies include cytokine release syndrome (CRS) and immune effector cell-associated neurotoxicity syndrome (ICANS), which can be life threatening if not timely treated. Early detection of these side effects is critical in order to address them. Therefore, patient health monitoring is critical for patients recovering from immunotherapy. Thus, there is a need for technological improvements in the field of patient health monitoring.

Under conventional approaches, patients recovering from immunotherapy are monitored by healthcare staff at regular intervals. The healthcare staff perform manual measurements of the patients' various vital signs to determine if the patients are experiencing any side effects. However, conventional approaches to monitoring patients can be inefficient and costly. For example, patients must remain under observation in a medical facility while being monitored. Furthermore, the patients' various vital signs are only periodically measured. Additionally, conventional approaches fail to predict whether a patient will experience side effects. Thus, conventional approaches fail to address these and other challenges arising in patient health monitoring.

An improved approach rooted in computer technology overcomes the foregoing and other challenges arising under conventional approaches. The present technology provides for a remote continuous monitoring system for patients. The monitoring system remotely and continuously monitors patients through one or more wearable sensors. The wearable sensors can measure patient vital signs, such as temperature, blood pressure, heart rate, respiratory rate, and the like. Based on measurements from the wearable sensors, the monitoring system can determine baseline vital signs for the patient. Based on the baseline vital signs, the monitoring system can determine vital sign thresholds that, when exceeded, indicate a likely onset of an adverse event. As the monitoring system measures the patient vital signs through the wearable sensors, the monitoring system can generate a notification (e.g., alarm) in response to a detection that a patient vital sign exceeds a corresponding vital sign threshold. The notification can allow the patient and healthcare service providers to appropriately respond to a likely onset of an adverse event. These features, and others relating to the present technology provided herein, allow patients to receive efficient care without requiring the patients to stay in a medical facility.

For example, with the present technology, a patient can recover from a procedure at home while being monitored through the remote continuous monitoring system. Prior to the procedure, the patient can wear a wearable sensor for a period of time to determine the patient's baseline vital signs. Based on the patient's baseline vital signs, the monitoring system can determine vital sign thresholds for the patient. For example, the monitoring system can apply personalized values to a biorhythm pattern determined based on the patient's baseline vitals. Based on the personalized values and the biorhythm pattern, the monitoring system can determine vital sign thresholds that follow the natural variations of the patient's baseline vitals and facilitate detection of a likely onset of side effects. Subsequent to the procedure, the patient can be monitored at home through the monitoring system via the wearable sensor. As the patient recovers, the monitoring system remotely and continuously measures the patient's vital signs and evaluates them against the vital sign thresholds. In this example, the monitoring system can also predict vital signs for the patient based on a history of the patient's vital signs and determine whether the predicted vital signs will exceed the vital sign thresholds. In response to a detection that the patient's vital signs or predicted vital signs exceed corresponding vital sign thresholds, the monitoring system can alert the patient and healthcare service providers of a likely onset of side effects. The patient and the healthcare service providers can then respond appropriately.

As illustrated in this example, the present technology allows for continuous monitoring of patient vital signs through a remote system. Advantageously, the present technology allows patients to be monitored outside a medical facility. Furthermore, through continuous monitoring of patient vital signs and predicting patient vital signs, the present technology allows for patients and healthcare service providers to proactively address side effects, providing improved healthcare to the patients. More details relating to the present technology are provided below.

Various aspects of the present technology can be implemented, in part or in whole, as software, hardware, or any combination thereof. In general, functionality as described herein can be associated with software, hardware, or any combination thereof. In some implementations, one or more functions, tasks, and/or operations described herein can be carried out or performed by software routines, software processes, hardware, and/or any combination thereof. In some instances, various aspects of the present technology can be, in part or in whole, implemented as software running on one or more computing devices or systems, such as on a server system or a client computing device. In some instances, various aspects of the present technology can be, in part or in whole, implemented within or configured to operate in conjunction with or be integrated with a server system (or service). Likewise, in some instances, various aspects of the present technology can be, in part or in whole, implemented within or configured to operate in conjunction with or be integrated with a client computing device. For example, the present technology can be implemented as or within a dedicated application (e.g., app), a program, or an applet running on a user computing device or client computing system. The application incorporating or implementing instructions for performing functionality of the present technology can be created by a developer. The application can be provided to or maintained in a repository. In some instances, the application can be uploaded or otherwise transmitted over a network (e.g., Internet) to the repository. For example, a computing system (e.g., server) associated with or under control of the developer of the application can provide or transmit the application to the repository. The repository can include, for example, an "app store" in which the application can be maintained for access or download by a user. In response to a command by the user to download the application, the application can be provided or otherwise transmitted over a network from the repository to a computing device associated with the user. For example, a computing system (e.g., server) associated with or under control of an administrator of the repository can cause or permit the application to be transmitted to the computing device of the user so that the user can install and run the application. The developer of the application and the administrator of the repository can be different entities in some cases but can be the same entity in other cases. Many variations are possible.

Figure 1B:
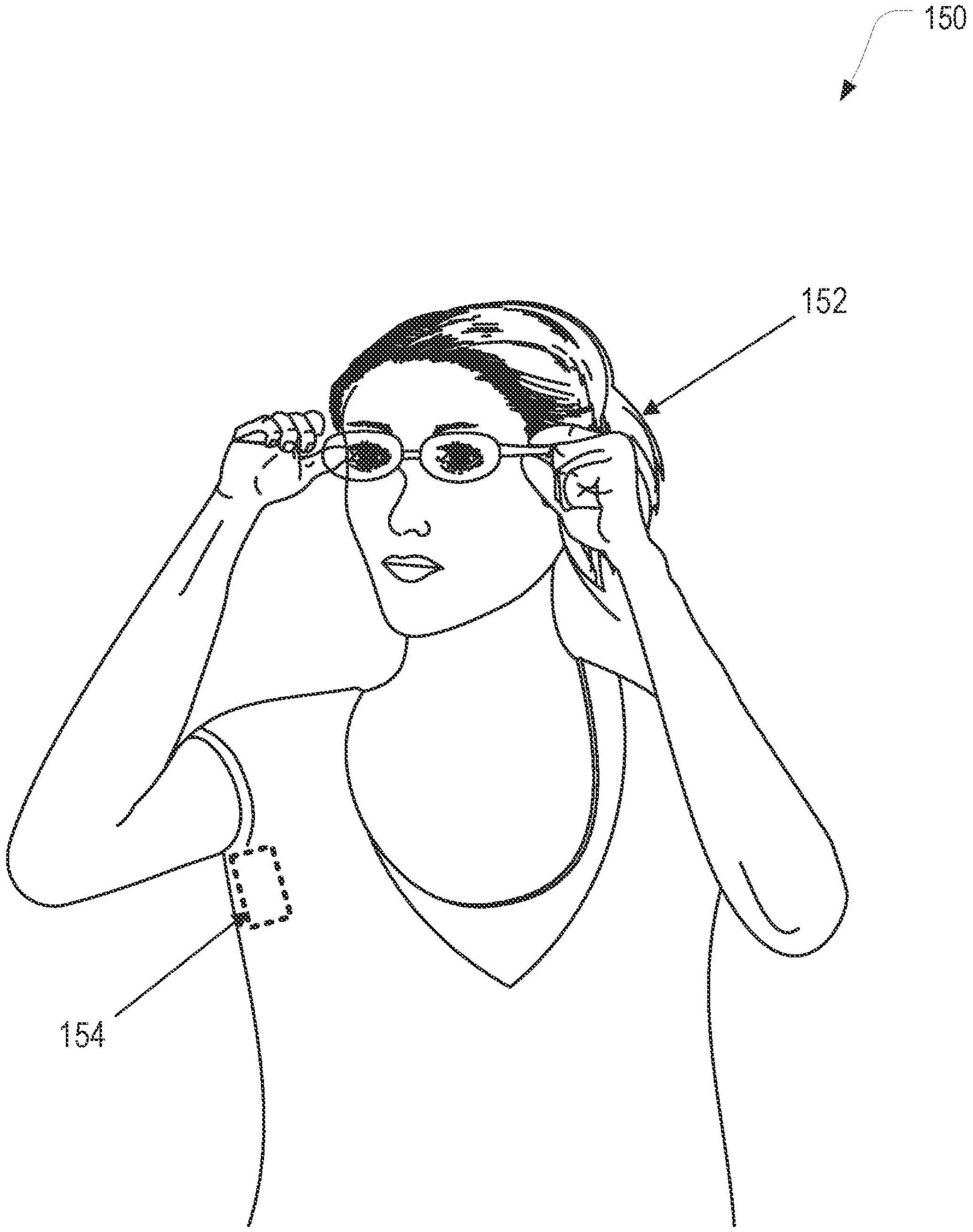

FIGS. 1A-1B illustrate examples of users with wearable sensors, according to various embodiments of the present technology. The examples illustrate one or more functionalities performed with the computing component 200 of FIG. 2. It should be understood that there can be additional, fewer, or alternative steps performed in similar or alternative orders, or in parallel, based on the various features discussed herein unless otherwise stated. All examples herein are provided for illustrative purposes, and there can be many variations and other possibilities.

FIG. 1A illustrates an example 100 of a user 102 with a wearable sensor 104. As illustrated in this example, the wearable sensor 104 is held against the skin of the user via an armband 106. The armband 106 may be adjustable to facilitate a secure fit that maintains the wearable sensor 104 against the skin and allows the wearable sensor 104 to take accurate measurements of patient vital signs. The wearable sensor 104 can include sensors on a side facing inward toward the arm of the user 102. The inward facing sensors can measure patient vital signs, such as skin temperature, heart rate, blood pressure, respiratory rate, and the like. In some cases, the wearable sensor 104 can include one or more sensors on a side facing outward away from the arm of the user 102. The outward facing sensors can measure ambient temperature, humidity, and the like. The wearable sensor 104 can include various connectivity functionalities. For example, the wearable sensor 104 can provide measurements over a Wi-Fi connection, a Bluetooth connection, a cellular connection, and the like. The wearable sensor 104 can include an audible alarm that can be activated by a remote continuous monitoring system.

FIG. 1B illustrates an example 150 of a user 152 with a wearable sensor 154. As illustrated in this example, the wearable sensor 154 is held against the skin of the user via an adhesive patch. The adhesive patch allows the wearable sensor 154 to be placed on the user 152 such that the wearable sensor 154 can measure axillary temperature among other patient vital signs. Like the wearable sensor 104 of FIG. 1A, the wearable sensor 154 can include sensors facing inward toward the body of the user 152 and sensors facing outward away from the body of the user 152. The inward facing sensors can measure patient vital signs, and the outward facing sensors can measure environmental measurements. The wearable sensor 154 can include various connectivity functionalities, such as Wi-Fi, Bluetooth, and cellular connections. The wearable sensor 154 can include an audible alarm that can be activated by a remote continuous monitoring system.

It should be understood that the present technology is not limited to a particular wearable sensor, and other wearable sensors in various forms are contemplated. For example, a wearable sensor can be held by a band around the body of a user. In some cases, multiple wearable sensors can be used to measure various patient vital signs at various locations on the body. Many variations are possible.

Figure 2:
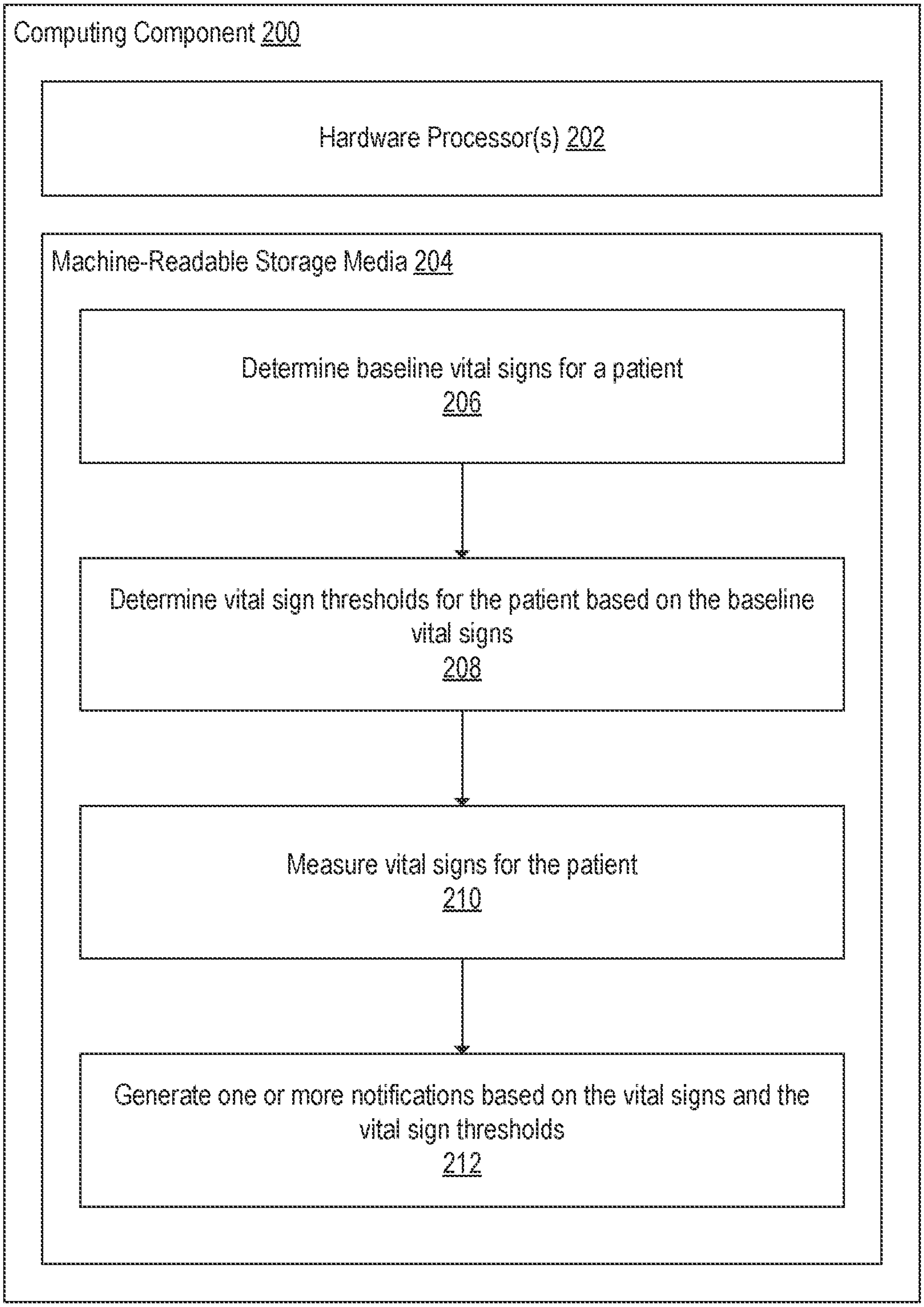
FIG. 2 illustrates an example system, according to various embodiments of the present technology.

FIG. 2 illustrates a computing component 200 that includes one or more hardware processor(s) 202 and machine-readable storage media 204 storing a set of machine-readable/machine-executable instructions that, when executed, cause the one or more hardware processor(s) 202 to perform an illustrative method for remote continuous monitoring, according to various aspects of the present technology. The computing component 200 may be, for example, the computing system 500 of FIG. 5. The one or more hardware processor(s) 202 may include, for example, the processor(s) 504 of FIG. 5 or any other processing unit described herein. The machine-readable storage media 204 may include the main memory 506, the read-only memory (ROM) 508, the storage device 510 of FIG. 5, and/or any other suitable machine-readable storage media described herein.

At block 206, the hardware processor(s) 202 may execute the machine-readable/machine-executable instructions stored in the machine-readable storage media 204 to determine baseline vital signs for a patient. The baseline vital signs for the patient can be indicative of the vital signs the patient exhibits in a normal state (e.g., prior to a procedure). The baseline vital signs for the patient can be based on measurements of the patient's vital signs over a period of time (e.g., 1 day, 1 week). During the period of time, the patient's vital signs can be measured continuously (e.g., every minute, every 5 minutes, every 15 minutes). The baseline vital signs for the patient can be determined based on the patient's vital signs measured during the period of time. For example, the baseline vital signs can be an average (or median) of the patient's vital signs measured during the period of time. In calculating the average of the patient's vital signs for the baseline vital signs, values outside a threshold deviation from the average of the patient's vital signs can be removed from the calculation of the average. In some instances, the average can be weighted so that the patient's vital signs that are measured more recently are weighted more than the patient's vital signs that are measured previously.

In some instances, baseline vital signs for different parts of the day can be determined based on the patient's vital signs measured during the different parts of the day. For example, a daytime baseline vital sign can be determined based on an average of the patient's vital signs measured during the daytime. A nighttime baseline vital sign can be determined based on an average of the patient's vital signs measured during the nighttime. As another example, baseline vital signs can be determined for each hour of the day based on respective averages of the patient's vital signs measured during each hour of the day. Many variations are possible.

In some instances, baseline vital signs can be determined as a biorhythm pattern. In general, a patient's vital signs change throughout the day. Based on measurements of the patient's vital signs as the patient's vital signs change throughout the day, a pattern or motif can be identified. Through a time series analysis of the patient's vital signs, the pattern or motif can be modeled. The time series analysis can identify peak values and bottom values for the patient's vital signs. The time series analysis can identify rates of change in the patient's vital signs at different times (e.g., every 15 minutes, every hour) throughout the day. For example, a pattern for a patient's temperature can include bottom values at night (e.g., when the patient is sleeping) and peak values during the day (e.g., when the patient is active). The pattern can include rates of change for the patient's temperature at each hour of the day. The pattern can have higher rates of change in the morning hours (e.g., when the patient is waking up) and in the evening hours (e.g., when the patient is falling asleep) and lower rates of change at night (e.g., when the patient is sleeping). In some instances, the pattern or motif can be modeled as a curve that rises and falls in accordance with the peak values, bottom values, and rates of change for the patient's vital signs.

In one aspect of the present technology, the baseline vital signs are based on measurements of patient vital signs and measurements of environmental elements, such as ambient temperature, humidity, $CO_2$ levels, weather conditions, and the like. By measuring environmental elements, patient vital signs affected by the environmental elements can be accounted for in determining baseline vital signs. For example, skin temperature can be affected by ambient temperature. By measuring skin temperature and ambient temperature, instances where lower than usual skin temperature measurements when ambient temperature is also low can be accounted for.

At block 208, the hardware processor(s) 202 may execute the machine-readable/machine-executable instructions stored in the machine-readable storage media 204 to determine vital sign thresholds for the patient based on the baseline vital signs. The present technology provides for various approaches to determining the vital sign thresholds. In a first approach, default values for vital sign thresholds can be provided. The default values can be established, for example, by a medical authority. For example, default values for temperature can be ±2° F. of a standard patient's baseline temperature (e.g., 98.6° F.). In this example, the upper temperature threshold can be 100.6° F., and the lower temperature threshold can be 96.6° F.

In a second approach, personalized values for vital sign thresholds can be determined based on baseline vital sign measurements of the patient. The personalized values can be predetermined values or adjusted by a healthcare service provider. For example, personalized values for temperature can be ±2° F. of a patient's baseline temperature. In this example, the patient's baseline temperature can be 97.8° F. The upper temperature threshold for the patient can be 99.8° F., and the lower temperature threshold for the patient can be 95.8° F. In some instances, the predetermined value for the upper threshold can be different from the predetermined value for the lower threshold. For example, personalized values for heart rate can be +20 bpm and −10 bpm of a patient's baseline heart rate. In this example, the patient's baseline heart rate can be 76 bpm. The upper heart rate threshold for the patient can be 96 bpm, and the lower heart rate threshold can be 66 bpm. The personalized values for vital sign thresholds can be adjusted. For example, the personalized values can be adjusted (e.g., increased, decreased) so that the vital sign thresholds are more sensitive or less sensitive to account for natural variations in the patient's vital signs. The personalized values can be adjusted to account for specific clinical scenarios and readjusted for different clinical scenarios. For example, personalized values for a patient with a clinical history of high risk health factors can be adjusted (e.g., decreased) to be more sensitive. The personalized values can be adjusted based on feedback from the patient or the healthcare service provider. For example, the personalized values can be adjusted (e.g., increased) to be less sensitive based on feedback from the patient of false positive notifications generated as a result of the personalized values for the vital sign thresholds.

In a third approach, vital sign thresholds can be determined based on patient biorhythm patterns. A patient's baseline vital signs can be determined as a biorhythm pattern that changes throughout the day. Upper thresholds for the patient's vital signs and lower thresholds for the lower patient's vital signs can be determined based on the biorhythm pattern. The upper thresholds and the lower thresholds can be determined based on a predetermined value, predetermined percentage, or other factor applied to the biorhythm pattern. For example, upper temperature thresholds and lower temperature thresholds for a patient can be ±2° F. or ±2% of the temperature of the patient's biorhythm pattern. In this example, if the patient's biorhythm pattern includes a baseline temperature of 97.8° F. at 3 AM, then the upper temperature threshold for the patient at 3 AM can be 99.8° F., and the lower temperature threshold for the patient at 3 AM can be 95.8° F. The predetermined values, predetermined percentages, or other factors applied to the biorhythm pattern can vary throughout the day based on the biorhythm pattern. For example, larger predetermined values or larger predetermined percentages can be applied to the patient's baseline vital signs for periods where the patient's biorhythm pattern exhibits larger variance, such as during the day. Smaller predetermined values or smaller predetermined percentages can be applied to the patient's baseline vital signs for periods where the patient's biorhythm pattern exhibits smaller variance, such as at night. For example, upper temperature thresholds and lower temperature thresholds for a patient can be ±2° F. of the temperature of the patient's biorhythm pattern from 11 AM to 6 PM, ±1.5° F. of the temperature of the patient's biorhythm pattern from 7 AM to 11 AM and from 6 PM to 10 PM, and ±1° F. of the temperature of the patient's biorhythm pattern from 10 PM to 7 AM. Many variations are possible.

In one aspect of the present technology, vital sign thresholds can be determined with respect to changes in the patient's biorhythm pattern. The patient's biorhythm pattern can include rates of change in the patient's vital signs throughout the day. The vital sign thresholds can include thresholds for rates of change in the patient's vital signs based on the patient's biorhythm pattern. For example, a patient's biorhythm pattern can include a temperature increase of 0.25° F. per hour in the morning (e.g., from 7 AM to 9 AM). Vital sign thresholds for the patient can include an upper temperature increase threshold of 0.35° F. per hour and a lower temperature increase threshold of 0.0° F. per hour in the morning. In this example, changes in the patient's vital signs, such as temperature increases over 0.35° F. per hour and temperature decreases can exceed the vital sign thresholds. The thresholds for rates of change can vary throughout the day based on the biorhythm pattern. For example, the thresholds for rates of change can be larger for periods where the patient's biorhythm pattern exhibits larger variance, such as during the day. The thresholds for rates of change can be smaller for periods where the patient's biorhythm pattern exhibits smaller variance, such as at night.

In a fourth approach, vital sign thresholds can be determined based on machine learning methodologies. A machine learning model can be trained to generate vital sign thresholds for a patient based on the patient's baseline vital signs. The machine learning model can be trained based on training data that includes instances of patient baseline vital signs and patient vital signs associated with onset of adverse events (e.g., side effects). Based on the training data, the machine learning model can be trained to generate vital sign thresholds that correspond with vital signs that indicate a likely onset of adverse events. In some instances, the machine learning model can be trained to consider various factors, such as clinical history, health risks, demographics, and the like. In some instances, the machine learning model can be trained to generate vital sign thresholds based on a patient's biorhythm pattern. For example, a patient's biorhythm pattern can be determined based on measurements of the patient's vital signs over a period of time. The patient's biorhythm pattern can be provided to a machine learning model. The machine learning model can generate vital sign thresholds based on the patient's biorhythm pattern. The vital sign thresholds can include, for example, upper thresholds and lower thresholds for the patient's vital signs. The vital sign thresholds generated by the machine learning model can increase and decrease over time based on the patient's biorhythm pattern. The vital sign thresholds generated by the machine learning model can include thresholds for rates of change that increase and decrease over time. Many variations are possible.

In one aspect of the present technology, vital sign thresholds can account for environmental elements. For example, a patient's baseline vital signs can be complemented with measurements of environmental elements. The vital sign thresholds can account for the environmental elements by increasing or decreasing based on the environmental elements. For example, the patient's baseline vital signs can be determined based on measurements of the patient's vital signs over a period of time. Measurements of environmental elements, such as ambient temperature, can complement the measurements of the patient's vital signs over the period of time. The measurements of the patient's vital signs and the measurements of the environmental elements can indicate, for example, that the patient's skin temperature is lower when the ambient temperature is lower, and that the patient's skin temperature is higher when the ambient temperature is higher. The temperature thresholds can increase and decrease based on the ambient temperature to account for the changes in the patient's body related to the ambient temperature.

It should be understood the present technology can apply various approaches in various combinations to determine vital sign thresholds. For example, a set of vital sign thresholds for a patient can include a subset of vital sign thresholds determined by a machine learning model and a subset of vital sign thresholds determined based on personalized values. Furthermore, the set of vital sign thresholds, including the vital sign thresholds determined by the machine learning model, can be adjusted based on feedback from the patient and the healthcare service provider. As further described below, a set of vital sign thresholds can include vital sign thresholds for predicted vital signs. The vital sign thresholds for predicted vital signs can include thresholds for probabilities, thresholds for time, and thresholds for vital sign measurements. For example, a set of vital sign thresholds for a patient can include vital sign thresholds for predicted vital signs determined in accordance with the approaches described herein. The set of vital sign thresholds can include, for example, a predicted temperature threshold that is exceeded if a predicted temperature exceeds 100.8° F., the predicted temperature is associated with a probability that exceeds 75%, and the predicted temperature is associated with a predicted time within 4 hours. The set of vital sign thresholds can include, as another example, a predicted temperature rate of change threshold that is exceeded if a predicted rate of change for temperature exceeds 0.35° F., exceeds 80% probability, and is within 3 hours. Many variations are possible.

At block 210, the hardware processor(s) 202 may execute the machine-readable/machine-executable instructions stored in the machine-readable storage media 204 to measure vital signs for the patient. The patient's vital signs can be measured through one or more wearable sensors. For example, the patient's vital signs can be measured through a sensor that adheres to the patient's skin with an adhesive patch. As another example, the patient's vital signs can be measured through a sensor that is held against the patient's skin by a band. The one or more wearable sensors can measure patient vital signs, such as temperature (e.g., skin temperature, axillary temperature), blood pressure, heart rate, respiratory rate, blood oxygen level, and the like. Measurement of vital signs for determining the patient's baseline vital signs and for monitoring the patient's vital signs can be performed through the same wearable sensors. In some instances, a group of measurements of vital signs can be grouped together to avoid outlier measurements triggering false positive. For example, a group of 15 measurements of vital signs can be averaged together.

In one aspect of the present technology, vital signs can be predicted for a patient to predict a likely onset of an adverse event. A machine learning model can be trained to predict vital signs based on a history of vital signs measured for a patient. The machine learning model can be trained based on training data that includes vital sign data from various patients in various use cases. Based on the training data, the machine learning model can be trained to generate predictions for vital signs based on a set of historical vital signs provided to the machine learning model. In some instances, the machine learning model can be trained for specific adverse events, such as particular side effects. For example, a machine learning model can be trained based on vital signs of immunotherapy patients recovering from a procedure. The machine learning model can be applied to a set of vital signs measured from a recovering immunotherapy patient. The set of vital signs can include, for example, the most recent two hours of vital signs measured from the recovering immunotherapy patient. The machine learning model can generate, based on the set of vital signs, predicted vital signs over a period of time (e.g., next 5 minutes, next 10 minutes, next hour, next several hours). In some instances, the machine learning model can generate a confidence score, or probability score, associated with the predicted vital signs that indicate a confidence, or probability, the predicted vital sign is accurate.

For example, a machine learning model can be trained to generated predicted vital signs for a patient over a period of time. The predicted vital signs can include, for example, predicted temperatures at 15 minute intervals over the next four hours. Each of the predicted temperatures can be associated with probability scores. For example, a predicted temperature for the next 15 minutes can have a probability of 0.95 (e.g., 95%) and another predicted temperature for the next 4 hours can have a probability of 0.65 (e.g., 65%). By considering the predicted vital signs over the period of time, a probability that an adverse event can be determined (e.g., when one or more predicted vital signs exceeds a corresponding vital sign threshold).

In some instances, a general machine learning model can be trained based on vital sign data from various use cases to predict vital signs for various use cases. The general machine learning model can be weighted to be sensitive and specific to particular adverse events. The weighting can be based on categorical values and/or real values associated with the vital sign data. The categorical values and/or real values can include critical blood based biomarkers, drug types, demographics, and the like. For example, the general machine learning model can be weighted to be specific to CRS cases by weighting the vital sign data that include categorical values and/or real values that indicate CRS cases. Many variations are possible.

At block 212, the hardware processor(s) 202 may execute the machine-readable/machine-executable instructions stored in the machine-readable storage media 204 to generate one or more notifications based on the vital signs and the vital sign thresholds. The one or more notifications can indicate a detection of a likely onset of an adverse event. For example, if the patient's vital signs exceed corresponding vital sign thresholds, a notification (e.g., alarm) can be generated to notify the patient and healthcare service providers of a likely onset of an adverse event. The notification can be provided, for example, through an audible alarm, through a mobile application, through a desktop application, through one or more emails, through a messaging application, and the like. The notification can allow the patient and the healthcare service providers to respond to the likely onset of the adverse event.

In one aspect of the present technology, the one or more notifications can be generated in response to the patient's vital signs exceeding corresponding vital sign thresholds, rates of change for the patient's vital signs exceeding corresponding thresholds for rates of change, deviations of the patient's vital signs from the patient's biorhythm pattern, and the like. For example, if the patient's temperature is higher than an upper temperature threshold, then a notification can be generated. In some instances, the one or more notifications can be generated in response to the patient's predicted vital signs exceeding corresponding vital sign thresholds. For example, if the patient's predicted temperature for the next four hours is higher than the upper temperature threshold for the next four hours, then a notification can be generated. In this example, the predicted vital signs can be associated with confidence scores, and the corresponding vital sign thresholds can be associated with confidence score thresholds. The one or more notifications can be generated if the confidence score associated with the patient's predicted temperature satisfies the confidence score threshold associated with the temperature threshold.

In one aspect of the present technology, the one or more notifications can be generated in response to a detected error. The detected error can include, for example, loss of connectivity with the wearable sensors, a loss of connectivity to the Internet, a loss of measurements from the wearable sensors, unusual measurements from the wearable sensors, and the like. For example, unusual measurements from the wearable sensors, such as patient vital signs that are outside normal vital sign thresholds, can indicate the wearable sensors have been removed from the patient.

In one aspect of the present technology, an interface can be provided through which patients and healthcare service providers can access patient vital signs and other information, provide feedback, send communications, and the like. For example, the patients and healthcare service providers can access a log of patient vital signs to evaluate the health of the patients during recovery. The patients and the healthcare service providers can access logs of detected errors to troubleshoot technical issues. The patients and the healthcare service providers can provide feedback for adjusting vital sign thresholds. The patients and the healthcare service providers can communicate through messages via the interface. For example, a patient can communicate that the patient is preparing to remove a wearable sensor so a healthcare service provider can be informed when a notification for a detected error is generated. The patients and the healthcare service providers can track use of healthcare products and order additional supplies (e.g., treatments) as appropriate. For example, a patient can receive a reminder to refill a prescription and order the refill through the interface. Many variations are possible.

In one aspect of the present technology, failsafe mechanisms can be provided to address situations where no notifications are generated, in cases where data flow is interrupted, in cases where a notification is missed (e.g., not read), and the like. When a notification is generated, a determination that the notification was received can be made based on, for example, read receipts that are generated when the notification is accessed. A failsafe mechanism can be triggered if a notification is not accessed within a threshold period of time. The failsafe mechanism can include, for example, an automated communication with alternative healthcare service providers and first line responders. For example, if a notification is not read by a healthcare service provider within an hour, another notification can be generated for an alternative healthcare service provider.

Figure 3A:
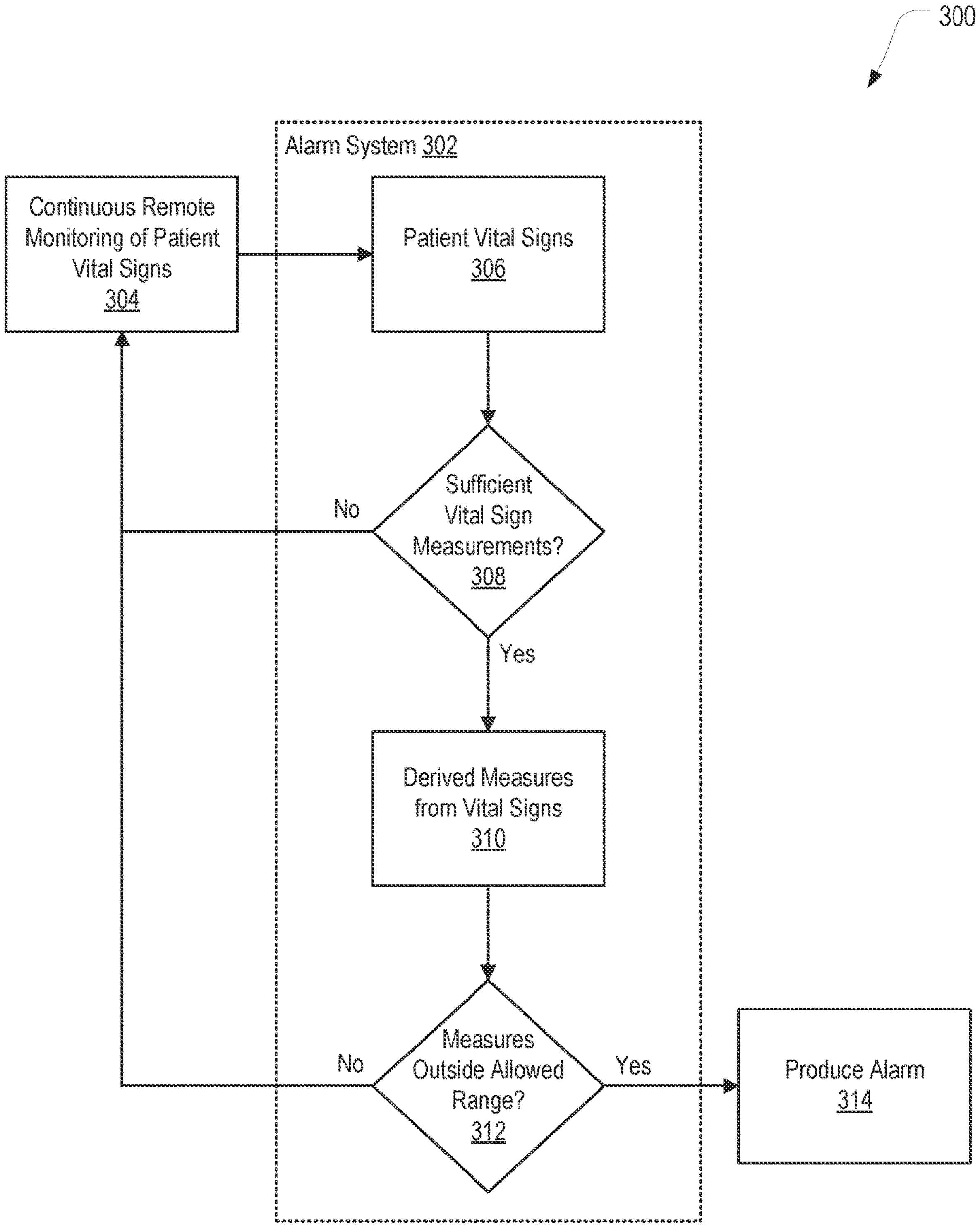
FIGS. 3A-3B illustrate example flows, according to various embodiments of the present technology.
Figure 3B:
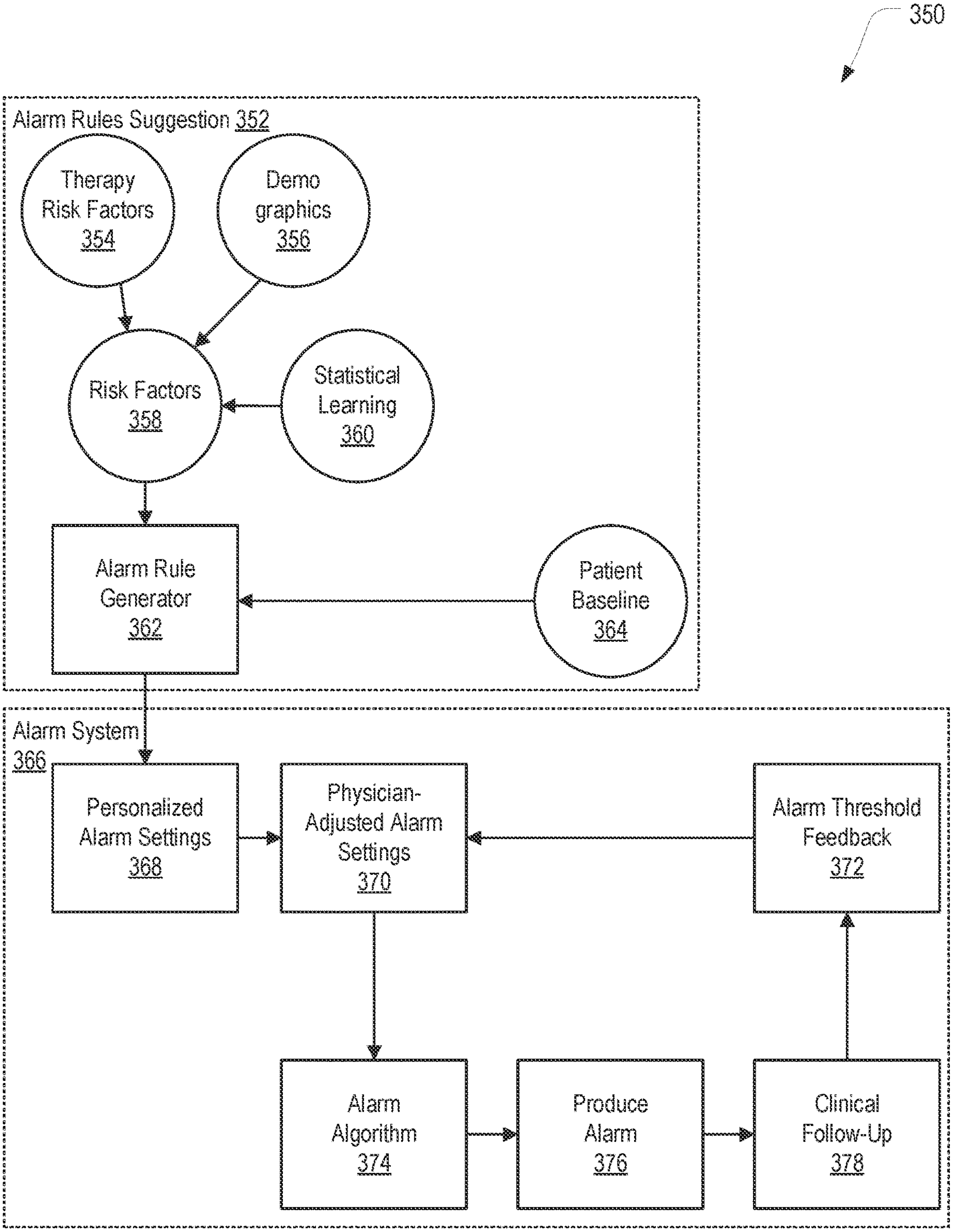

FIGS. 3A-3B illustrate example flows, according to various embodiments of the present technology. The example flows can be facilitated by one or more functionalities performed by the computing component 200 of FIG. 2. It should be understood that there can be additional, fewer, or alternative steps performed in similar or alternative orders, or in parallel, based on the various features discussed herein unless otherwise stated. All examples herein are provided for illustrative purposes, and there can be many variations and other possibilities.

FIG. 3A illustrates an example flow 300 associated with use of a remote continuous monitoring system. The remote continuous monitoring system includes an alarm system 302 that determines when an alarm is to be produced to indicate a likely onset of an adverse event. At block 304, continuous remote monitoring of patient vital signs is performed. For example, continuous remote monitoring of axillary temperature can be performed through a wearable sensor. At 306, patient vital signs over a period of time are evaluated. For example, the axillary temperature over a previous number of minutes can be evaluated. In this example, patient vital signs can be grouped for evaluation in configurable time windows. By using a grouping of patient vital signs, outlier measurements can be avoided. At 308, a determination is made as to whether there are sufficient vital sign measurements to evaluate. In this example, a minimum number of measurements can be considered to avoid unreliability due to missing measurements. If there are not sufficient vital sign measurements to evaluate, then at block 304, continuous remote monitoring of patient vital signs is performed. If there are sufficient vital sign measurements to evaluate, then at block 310, measures can be derived from the patient vital signs. For example, measure of central tendency (e.g., average) and rate of change can be derived from the patient vital signs. In this example, multiple statistical options can be applied to the patient vital signs. For example, a range, a linear gradient of change, a change with respect to a previous time window, a change with respect to standard deviation, a breach of an absolute value, and the like can be applied. At block 312, a determination is made as to whether the measure is outside of an allowed range. For example, the axillary temperature or a rate of change of the axillary temperature can exceed axillary temperature thresholds. If the measure is not outside of the allowed range, then at block 304, continuous remote monitoring of patient vital signs is performed. If the measure is outside of the allowed range, then at block 314, an alarm is produced.

FIG. 3B illustrates an example flow 350 associated with use of a remote continuous monitoring system. The remote continuous monitoring system includes an alarm rules suggestion module 352 and an alarm system 366. At block 362, an alarm rule generator can generate rules (e.g., vital sign thresholds) based on a patient baseline 364 and risk factors 358. The risk factors 358 can include therapy risk factors 354, demographics 356, and statistical learning 360. Therapy risk factors 354 can include, for example, risk factors associated with a particular therapy, dosing, delivery method, and the like. Demographics 356 can include, for example, age, gender, tumor burden, and the like. Statistical learning 360 can include, for example, tendencies derived from past physiological data, such as vital sign data, temperature, heart rate, respiratory rate, blood oxygen, and the like. At 368, personalized alarm settings are generated. For example, the personalized alarm settings can include personalized values for vital sign thresholds. At 370, the personalized alarm settings are adjusted by a physician. For example, the physician can adjust the vital sign thresholds to increase or decrease sensitivity. At 374, an alarm algorithm is used to determine whether to generate an alarm to indicate a likely onset of an adverse event. At 376, an alarm is produced. For example, the alarm can indicate that a patient vital sign exceeds a corresponding patient vital sign threshold, indicating a likely onset of an adverse event. At 378, a clinical follow up between the patient and the physician is performed. The patient and the physician can discuss, for example, the cause of the alarm. At 372, alarm threshold feedback is provided. For example, the physician can provide feedback to adjust the vital sign thresholds to increase or decrease sensitivity (e.g., to reduce false alarms).

Figure 4:
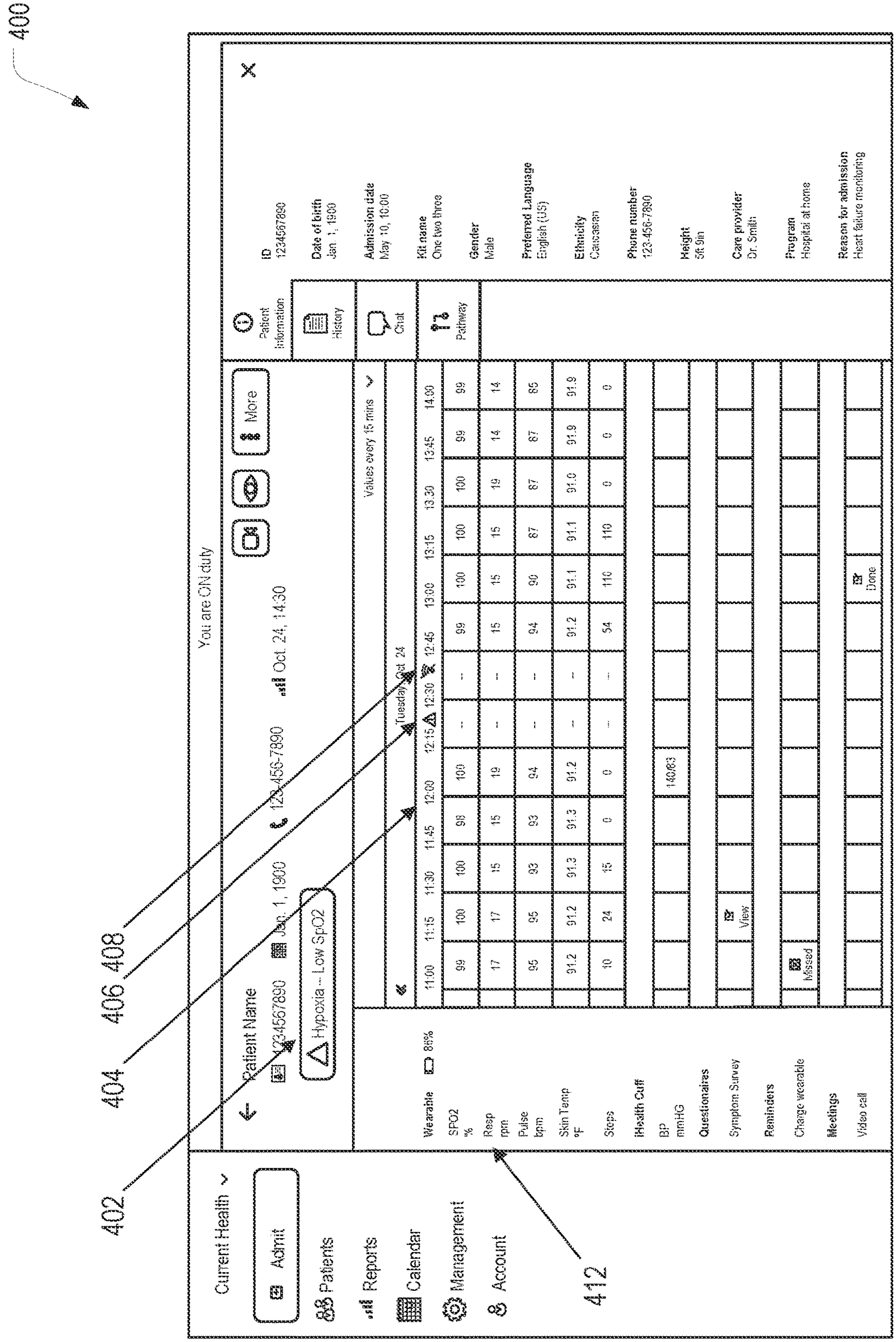
FIG. 4 illustrates an example interface, according to various embodiments of the present technology.

FIG. 4 illustrates an example interface 400, according to various embodiments of the present technology. The example interfaces can be provided in association with one or more functionalities performed by the computing component 200 of FIG. 2. It should be understood that there can be additional, fewer, or alternative steps performed in similar or alternative orders, or in parallel, based on the various features discussed herein unless otherwise stated. All examples herein are provided for illustrative purposes, and there can be many variations and other possibilities.

As illustrated in FIG. 4, the example interface 400 provides various patient information for a patient undergoing recovery from a procedure. The interface 400 includes an alert 402 to indicate an adverse event (e.g., hypoxia) has been previously detected. In response to an interaction with the alert 402, the interface 400 can provide patient vital signs measured around the time of the adverse event. The interface 400 provides a listing 412 of recorded information, including patient vital signs (e.g., blood oxygen, respiratory rate, heart rate, skin temperature, blood pressure) and a log of patient activity, including past surveys, reminders received, video meetings, and the like. The interface 400 includes a timeline 404 associated with the recorded information, providing, for example, the times at which the patient vital signs were measured. The interface 400 includes a first alert 406 that indicates a time when no patient vital signs were measured. This may indicate, for example, that the wearable sensor was removed or ran out of power. The interface 400 includes a second alert 408 that indicates a time of no connectivity. This may indicate, for example, that Internet connectivity was lost.

It is contemplated that there can be many other uses, applications, and/or variations associated with the various embodiments of the present technology. For example, various embodiments of the present technology can learn, improve, and/or be refined over time.

Hardware Implementation

Figure 5:
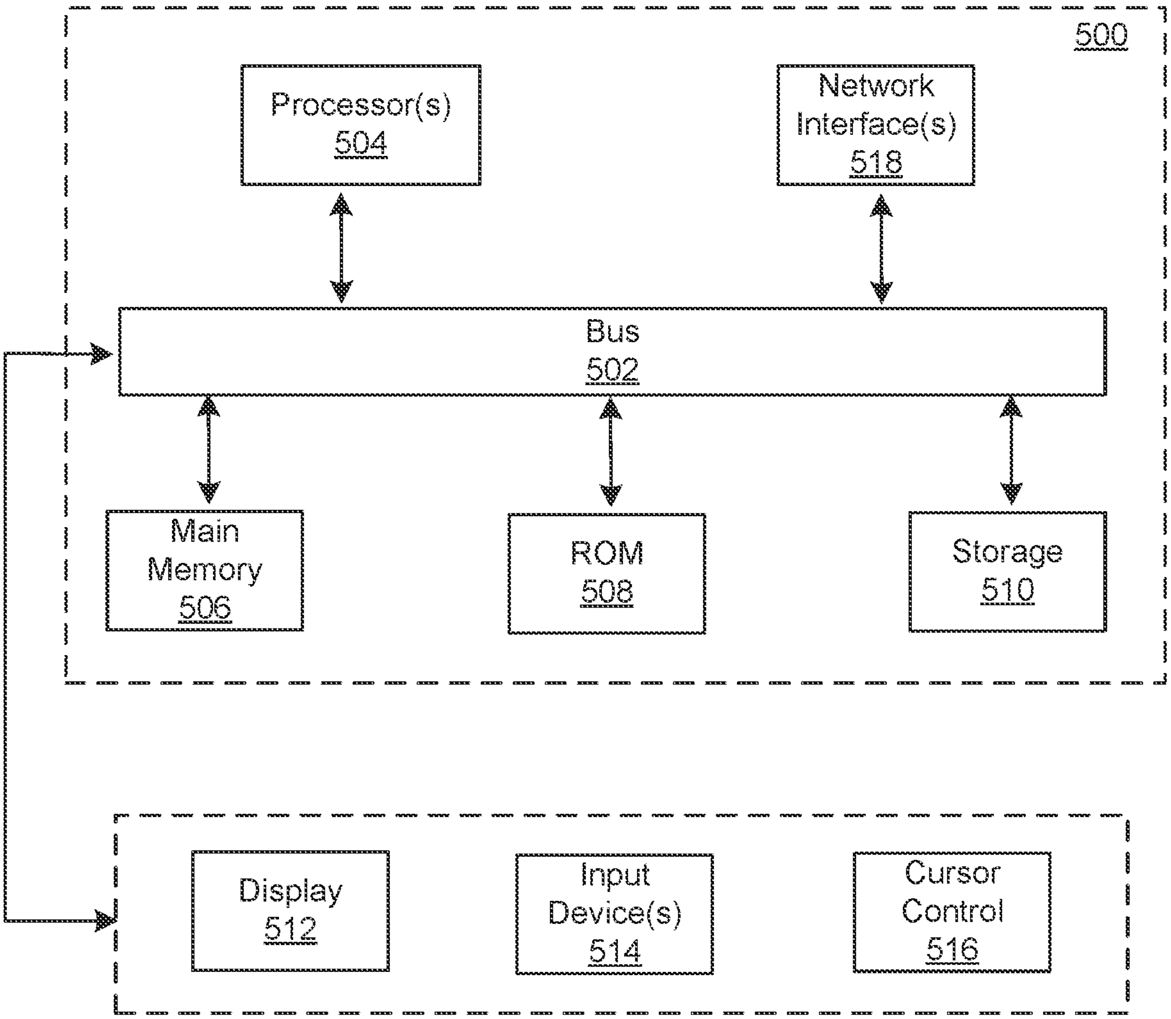
FIG. 5 illustrates an example computer system, according to various embodiments of the present technology.

The foregoing processes and features can be implemented by a wide variety of machine and computer system architectures and in a wide variety of network and computing environments. FIG. 5 illustrates an example computing system 500 in which various features described herein may be implemented. The computing system 500 includes a bus 502 or other communication mechanism for communicating information, one or more hardware processor(s) 504 coupled with bus 502 for processing information. Hardware processor(s) 504 may be, for example, one or more general purpose microprocessors.

The computing system 500 also includes a main memory 506, such as a random-access memory (RAM), cache and/or other dynamic storage devices, coupled to bus 502 for storing information and instructions to be executed by hardware processor(s) 504. Main memory 506 also may be used for storing temporary variables or other intermediate information during execution of instructions to be executed by hardware processor(s) 504. Such instructions, when stored in storage media accessible to hardware processor(s) 504, render computing system 500 into a special-purpose machine that is customized to perform the operations specified in the instructions.

The computing system 500 further includes a read only memory (ROM) 508 or other static storage device coupled to bus 502 for storing static information and instructions for hardware processor(s) 504. A storage device 510, such as a magnetic disk, optical disk, or USB thumb drive (Flash drive), etc., is provided and coupled to bus 502 for storing information and instructions.

The computing system 500 may be coupled via bus 502 to a display 512, such as a liquid crystal display (LCD) (or touch screen), for displaying information to a computer user. An input device 514, including alphanumeric and other keys, is coupled to bus 502 for communicating information and command selections to hardware processor(s) 504. Another type of user input device is cursor control 516, such as a mouse, a trackball, or cursor direction keys for communicating direction information and command selections to hardware processor(s) 504 and for controlling cursor movement on display 512. In some embodiments, the same direction information and command selections as cursor control may be implemented via receiving touches on a touch screen without a cursor.

The computing system 500 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computing system 500 may implement the techniques described herein using customized hard-wired logic, one or more ASICs or FPGAs, firmware and/or program logic which in combination with the computer system causes or programs computing system 500 to be a special-purpose machine. According to one embodiment, the techniques herein are performed by computing system 500 in response to hardware processor(s) 504 executing one or more sequences of one or more instructions contained in main memory 506. Such instructions may be read into main memory 506 from another storage medium, such as storage device 510. Execution of the sequences of instructions contained in main memory 506 causes hardware processor(s) 504 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 510. Volatile media includes dynamic memory, such as main memory 506. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 502. Transmission media can also take the form of acoustic or light waves, such as those generated during radio-wave and infra-red data communications.

The computing system 500 also includes a communication interface 518 coupled to bus 502. Communication interface 518 provides a two-way data communication coupling to one or more network links that are connected to one or more local networks. For example, communication interface 518 may be an integrated services digital network (ISDN) card, cable modem, satellite modem, or a modem to provide a data communication connection to a corresponding type of telephone line. As another example, communication interface 518 may be a local area network (LAN) card to provide a data communication connection to a compatible LAN (or WAN component to communicated with a WAN). Wireless links may also be implemented. In any such implementation, communication interface 518 sends and receives electrical, electromagnetic or optical signals that carry digital data streams representing various types of information.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, software, or a combination thereof. For example, one or more processors, controllers, ASICs, PLAS, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 800.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

In general, routines executed to implement the embodiments of the invention can be implemented as part of an operating system or a specific application, component, program, object, module, or sequence of instructions referred to as "programs" or "applications." For example, one or more programs or applications can be used to execute any or all of the functionality, techniques, and processes described herein. The programs or applications typically comprise one or more instructions set at various times in various memory and storage devices in the machine and that, when read and executed by one or more processors, cause the computing system 700 to perform operations to execute elements involving the various aspects of the embodiments described herein.

The executable routines and data may be stored in various places, including, for example, ROM, volatile RAM, non-volatile memory, and/or cache memory. Portions of these routines and/or data may be stored in any one of these storage devices. Further, the routines and data can be obtained from centralized servers or peer-to-peer networks. Different portions of the routines and data can be obtained from different centralized servers and/or peer-to-peer networks at different times and in different communication sessions, or in a same communication session. The routines and data can be obtained in entirety prior to the execution of the applications. Alternatively, portions of the routines and data can be obtained dynamically, just in time, when needed for execution. Thus, it is not required that the routines and data be on a machine-readable medium in entirety at a particular instance of time.

While embodiments have been described fully in the context of computing systems, those skilled in the art will appreciate that the various embodiments are capable of being distributed as a program product in a variety of forms, and that the embodiments described herein apply equally regardless of the particular type of machine-or computer-readable media used to actually effect the distribution.

Alternatively, or in combination, the embodiments described herein can be implemented using special purpose circuitry, with or without software instructions, such as using Application-Specific Integrated Circuit (ASIC) or Field-Programmable Gate Array (FPGA). Embodiments can be implemented using hardwired circuitry without software instructions, or in combination with software instructions. Thus, the techniques are limited neither to any specific combination of hardware circuitry and software, nor to any particular source for the instructions executed by the data processing system.

For purposes of explanation, numerous specific details are set forth in order to provide a thorough understanding of the description. It will be apparent, however, to one skilled in the art that embodiments of the technology can be practiced without these specific details. In some instances, modules, structures, processes, features, and devices are shown in block diagram form in order to avoid obscuring the description or discussed herein. In other instances, functional block diagrams and flow diagrams are shown to represent data and logic flows. The components of block diagrams and flow diagrams (e.g., modules, engines, blocks, structures, devices, features, etc.) may be variously combined, separated, removed, reordered, and replaced in a manner other than as expressly described and depicted herein.

Reference in this specification to "one embodiment," "an embodiment," "other embodiments," "another embodiment," "in various embodiments," or the like means that a particular feature, design, structure, or characteristic described in connection with the embodiment is included in at least one embodiment of the technology. The appearances of, for example, the phrases "according to an embodiment," "in one embodiment," "in an embodiment," "in various embodiments," or "in another embodiment" in various places in the specification are not necessarily all referring to the same embodiment, nor are separate or alternative embodiments mutually exclusive of other embodiments. Moreover, whether or not there is express reference to an "embodiment" or the like, various features are described, which may be variously combined and included in some embodiments but also variously omitted in other embodiments. Similarly, various features are described which may be preferences or requirements for some embodiments but not other embodiments.

Although embodiments have been described with reference to specific exemplary embodiments, it will be evident that the various modifications and changes can be made to these embodiments. Accordingly, the specification and drawings are to be regarded in an illustrative sense rather than in a restrictive sense. The foregoing specification provides a description with reference to specific exemplary embodiments. It will be evident that various modifications can be made thereto without departing from the broader spirit and scope as set forth in the following claims. The specification and drawings are, accordingly, to be regarded in an illustrative sense rather than a restrictive sense.

Although some of the drawings illustrate a number of operations or method steps in a particular order, steps that are not order dependent may be reordered and other steps may be combined or omitted. While some reordering or other groupings are specifically mentioned, others will be apparent to those of ordinary skill in the art and so do not present an exhaustive list of alternatives. Moreover, it should be recognized that the stages could be implemented in hardware, firmware, software, or any combination thereof.

It should also be understood that a variety of changes may be made without departing from the essence of the invention. Such changes are also implicitly included in the description. They still fall within the scope of this invention. It should be understood that this technology is intended to yield a patent covering numerous aspects of the invention, both independently and as an overall system, and in both method and apparatus modes.

Further, each of the various elements of the invention and claims may also be achieved in a variety of manners. This technology should be understood to encompass each such variation, be it a variation of an embodiment of any apparatus embodiment, a method or process embodiment, or even merely a variation of any element of these.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible in accordance with the following claims.

The language used herein has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the technology of the embodiments of the invention is intended to be illustrative, but not limiting, of the scope of the invention, which is set forth in the following claims.

What is claimed is:

1. A method for remote monitoring of an immunotherapy patient's vital signs after receiving an immunotherapy treatment to promptly detect an indication of a likely onset of adverse events from known side effects of the immunotherapy treatment without requiring the patient to remain in a treatment facility for observation, comprising:

determining over a period of time prior to the treatment, by a computing system, a patient's baseline values for a set of vital signs, the set of vital signs including vital signs relevant to determining the likely onset of adverse events from known side effects of the immunotherapy treatment;

determining, and storing in the computing system, personalized values for vital sign thresholds based on the patient's baseline values for the set of vital signs, the vital sign threshold values being indicative of the likely onset of one or more known adverse events associated with the treatment, the vital sign thresholds including a first predetermined amount above and/or a second predetermined amount below the patient's respective baseline vital sign values, wherein the personalized values for vital sign thresholds include patient-specific upper and lower thresholds for one or more of the set of vital signs, defined as predetermined offsets from the patient's baseline values for a corresponding vital sign;

generating, via an alarm rule generator, alarm rules based on the vital sign thresholds;

remotely measuring, after the treatment, by one or more wearable sensors, first vital signs for the patient;

determining, by the computing computer system, if vital signs measured after the treatment exceed at least one of the corresponding patient vital sign thresholds; and generating, by the computing system, one or more notifications based on the alarm rules.

2. The method of claim 1, wherein determining the patient's baseline values for a set of vital signs comprises:

measuring, prior to the patient undergoing the treatment, the patient's baseline values for the set of vital signs by the computing system, over a period of time; and determining, by the computing system, an average of the baseline values for the set of vital signs over the period of time.

3. The method of claim 1, wherein determining the patient's baseline values for a set of vital signs comprises:

measuring, prior to the measuring first vital signs, by the computing system, second vital signs for the patient over a period of time; and determining, by the computing system, a biorhythm pattern for the patient based on the second vital signs, wherein the vital sign thresholds are based on the biorhythm pattern.

4. The method of claim 1, wherein determining the patient's baseline values for a set of vital signs comprises:

measuring, prior to the measuring first vital signs, by the computing system, second vital signs for the patient over a period of time; and measuring, prior to the measuring the first vital signs, by the computing system, environmental elements.

5. The method of claim 1, wherein determining the vital sign thresholds for the patient comprises:

determining, by the computing system, an upper vital sign threshold and a lower vital sign threshold based on one or more predetermined values for the vital sign thresholds of the patient; and adjusting, by the computing system, the upper vital sign threshold and the lower vital sign threshold based on feedback.

6. The method of claim 1, wherein determining the vital sign thresholds for the patient comprises:

determining, by the computing system, upper vital sign thresholds and lower vital sign thresholds based on an application of one or more predetermined values to a biorhythm pattern associated with the patient.

7. The method of claim 1, wherein determining the vital sign thresholds for the patient comprises:

providing, by the computing system, the baseline vital signs to a machine learning model; and determining, by the computing system, upper vital sign thresholds and lower vital sign thresholds based on the machine learning model.

8. The method of claim 1, wherein determining the vital sign thresholds for the patient comprises:

determining, by the computing system, an upper threshold for a rate of change in a vital sign and a lower threshold for the rate of change in the vital sign based on rates of changes determined from the baseline vital signs.

9. The method of claim 1, further comprising:

generating, by the computing system, predicted vital signs based on the vital signs for the patient, wherein the one or more notifications are generated based on the predicted vital signs exceeding a corresponding vital sign threshold.

10. The method of claim 1, wherein the one or more notifications comprise an alert to a detection of an onset of an adverse event.

11. The method of claim 1, wherein determining vital sign thresholds for the patient comprises determining patient-specific vital signs thresholds for the patient after the patient has undergone an immunotherapy treatment and the patient-specific vital sign thresholds are determined based on vital sign values that are likely to indicate known adverse events associated with the immunotherapy treatment, including cytokine release syndrome (CRS) and/or immune effector cell-associated neurotoxicity syndrome (ICANS).

12. A system for remote monitoring of an immunotherapy patient's vital signs after receiving an immunotherapy treatment to detect an indication of a likely onset of adverse events from known side effects of the immunotherapy treatment without requiring the patient to remain in a treatment facility for observation, comprising:

at least one processor; and a memory storing instructions that, when executed, cause the system to perform:

determining over a period of time prior to the treatment, a patient's baseline values for a set of vital signs, the set of vital signs including vital signs relevant to determining the likely onset of adverse events from known side effects of the immunotherapy treatment;

determining and storing, personalized values for vital sign thresholds based on the patient's baseline values for the set of vital signs, the vital sign thresholds being indicative of the likely onset of one or more known adverse events associated with the treatment, the vital sign thresholds including a first predetermined amount above and/or a second predetermined amount below the patient's respective baseline vital sign values, wherein the personalized values for vital sign thresholds include patient-specific upper and lower thresholds for one or more of the set of vital signs, defined as predetermined offsets from the patient's baseline values for a corresponding vital sign;

generating, via an alarm rule generator, alarm rules based on the vital sign thresholds;

remotely measuring, after the treatment, by one or more wearable sensors, first vital signs for the patient;

determining if vital signs measured after the treatment exceed at least one of the corresponding patient vital sign thresholds; and generating one or more notifications based on the alarm rules.

13. The system of claim 12, wherein determining the patient's baseline values for a set of vital signs comprises:

measuring, prior to the measuring first vital signs, second vital signs for the patient over a period of time; and determining a biorhythm pattern for the patient based on the second vital signs, wherein the vital sign thresholds are based on the biorhythm pattern.

14. The system of claim 12, wherein determining the vital sign thresholds for the patient comprises:

determining upper vital sign thresholds and lower vital sign thresholds based on an application of one or more predetermined values to a biorhythm pattern associated with the patient.

15. The system of claim 12, wherein determining the vital sign thresholds for the patient comprises:

providing the baseline vital signs to a machine learning model; and determining upper vital sign thresholds and lower vital sign thresholds based on the machine learning model.

16. The system of claim 12, wherein the instructions cause the system to further perform:

generating predicted vital signs based on the vital signs of the patient, wherein the one or more notifications are generated based on the predicted vital signs exceeding a corresponding vital sign threshold.

17. A non-transitory computer-readable storage medium for remote monitoring of an immunotherapy patient's vital signs after receiving an immunotherapy treatment to detect an indication of a likely onset of adverse events from known side effects of the immunotherapy treatment without requiring the patient to remain in a treatment facility for observation including instructions that, when executed, cause a computing system to perform:

determining over a period of time prior to the treatment, a patient's baseline values for a set of vital signs, the set of vital signs including vital signs relevant to determining the likely onset of adverse events from known side effects of the immunotherapy treatment;

determining and storing, personalized values for vital sign thresholds based on the patient's baseline values for the set of vital signs, the vital sign thresholds being indicative of the likely onset of one or more known adverse events associated with the treatment, the vital sign thresholds including a first predetermined amount above and/or a second predetermined amount below the patient's respective baseline vital sign values, wherein the personalized values for vital sign thresholds include patient-specific upper and lower thresholds for one or more of the set of vital signs, defined as predetermined offsets from the patient's baseline values for a corresponding vital sign;

generating, via an alarm rule generator, alarm rules based on the vital sign thresholds;

remotely measuring, after the treatment, by one or more wearable sensors, first vital signs for the patient;

determining if the vital signs measured after the treatment exceed at least one of the corresponding patient vital sign thresholds; and generating one or more notifications based on the alarm rules.

18. The non-transitory computer-readable storage medium of claim 17, wherein determining the patient's baseline values for a set of vital signs comprises:

measuring, prior to the measuring first vital signs, second vital signs for the patient over a period of time; and determining a biorhythm pattern for the patient based on the second vital signs, wherein the vital sign thresholds are based on the biorhythm pattern.

19. The non-transitory computer-readable storage medium of claim 17, wherein determining the vital sign thresholds for the patient comprises:

determining upper vital sign thresholds and lower vital sign thresholds based on an application of one or more predetermined values to a biorhythm pattern associated with the patient.

20. The non-transitory computer-readable storage medium of claim 17, wherein determining the vital sign thresholds for the patient comprises:

providing the baseline vital signs to a machine learning model; and determining upper vital sign thresholds and lower vital sign thresholds based on the machine learning model.

21. The non-transitory computer-readable storage medium of claim 17, wherein the instructions cause the computing system to further perform:

generating predicted vital signs based on the vital signs of the patient, wherein the one or more notifications are generated based on the predicted vital signs exceeding a corresponding vital sign threshold.

* * * * *